Figure 1:
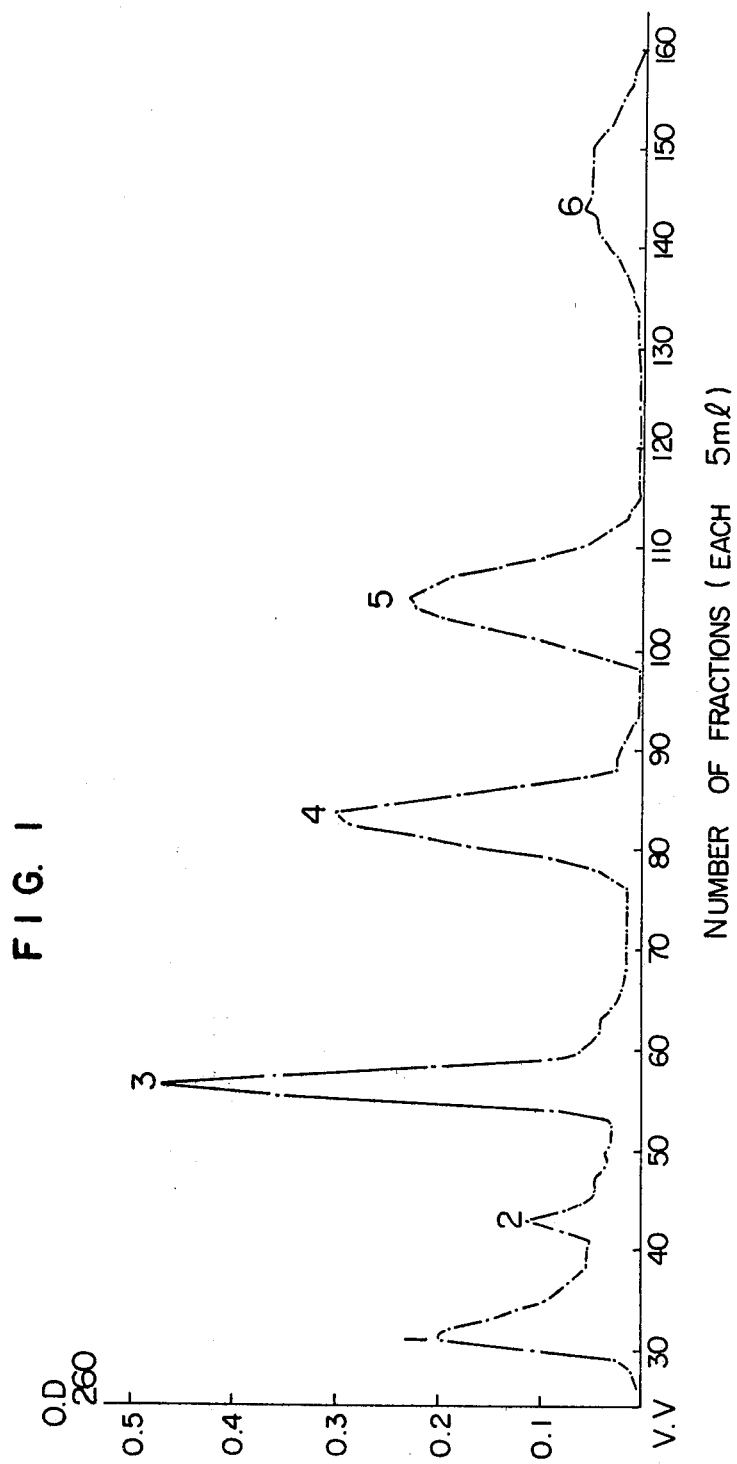

United States Patent [19]

Saikawa et al.

[11] 4,370,316
[45] Jan. 25, 1983

[54] PHARMACEUTICAL COMPOSITION COMPRISING EXTRACT FROM POISON POUCH CONTENTS OF BEE USEFUL FOR TREATING DECREASED IMMUNITY

[75] Inventors: Isamu Saikawa; Takashi Yasuda; Shohachi Murakami, all of Toyama; Toyoo Maeda, Kanazawa; Akira Yotsuji, Toyama; Masahiro Takahata, Toyama; Hisatsugu Tsuda, Toyama; Hidetada Mikami; Hiroshi Sakai, both of Takaoka; Toshinori Ohashi, Hitachi, all of Japan

[73] Assignee: Toyama Chemical Company, Ltd., Tokyo, Japan

[21] Appl. No.: 147,530

[22] Filed: May 7, 1980

[30] Foreign Application Priority Data

May 10, 1979 [JP] Japan .................................. 54-57461

[51] Int. Cl.$^3$ ............................................. A61K 35/58
[52] U.S. Cl. ......................................... 424/98; 424/95
[58] Field of Search .................................... 424/95, 98

[56] References Cited

FOREIGN PATENT DOCUMENTS 29-991  2/1954  Japan .

OTHER PUBLICATIONS

Dyer, "Index of Tumor Chemotherapy" USPHS 3/49, pp. 10, 11, 180, 232, 296 & 328.
Yoannovitch et al., Bull. de l'Académie de Médecine (Paris) 107; pp. 892–893 (1932).
Natale, Tumori (Milan) 29; pp. 324–341 and 344–348 (1935).
Chem. Abstr. 36 (1942) 2090$^8$.
Chem. Abstr. 50 (1956) 12296$^c$.
Chem. Abstr. 44 (1950) 4202$f$.
Chem. Abstr. 46 (1952) 3644$^a$.
Chem. Abstr. 48 (1954) 9418 $f$.
Chem. Abstr. 49 (1955) 4882$g$.
Chem. Abstr. 55 (1961) 15841-2.
Chem. Abstr. 64 (1966) 6403$^a$.
Chem. Abstr. 69 (1968) 58120$^e$.
New Drugs in Japan, vol. 4, 130.

*Primary Examiner*—Sam Rosen
*Attorney, Agent, or Firm*—Oblon, Fisher, Spivak, McClelland & Maier

[57] ABSTRACT

A method for treating a host mammal having a decreased immunity, comprising administering to said host mammal an immunostimulating effective amount of the deproteinized extract from the poison pouch contents of bee B-T, is disclosed.

1 Claim, 6 Drawing Figures

PHARMACEUTICAL COMPOSITION COMPRISING EXTRACT FROM POISON POUCH CONTENTS OF BEE USEFUL FOR TREATING DECREASED IMMUNITY

This invention relates to an immunostimulating agent comprising a component obtained by deproteinizing an extract from the poison pouch contents of a bee, and to a carcinostatic agent comprising said component and a carcinostatic substance, and to an antibacterial agent comprising said component and an antibacterial substance (said component is hereinafter referred to as the B-T).

Recently, bacterially infected diseases difficult to cure (Opportunitic infection) owing to a decrease in self-immunity have been reported. It is known that the decrease in human immunity is caused by functional diseases such as primary immunodeficiencies, congenital complement-deficiencies, and the like, various diseases such as malignant tumor disease, leukemia, malignant lymphoma, virally infectious diseases and the like; and administration of drugs such as carcinostatic agents, immunosuppressants, antispasmodics, adrenocortical hormone preparations and the like; radiotherapy, etc.

Therefore, in order to treat various cancer diseases, viral infection and bacterially infected diseases difficult to cure there have been investigated a method by which a drug stimulating a self-immunity is administered and a method by which together with a curative drug, a drug having an immunostimulating activity which enhances the activity of the curative drug is administered.

In order to develop said immunostimulating substance, the present inventors have conducted extensive research, and it has consequently been found that the B-T has an excellent immunostimulating activity and has an excellent effect in treating bacterially infected diseases, and that when the B-T is used together with carcinostatic substances or antibacterial substances, the carcinostatic and antibacterial effects of the agents are remarkably increased.

According to this invention, there is provided an immunostimulating agent comprising the B-T.

This invention further provides a carcinostatic agent comprising the B-T and a carcinostatic substance.

This invention further provides an antibacterial agent comprising the B-T and an antibacterial substance.

Figure 2:
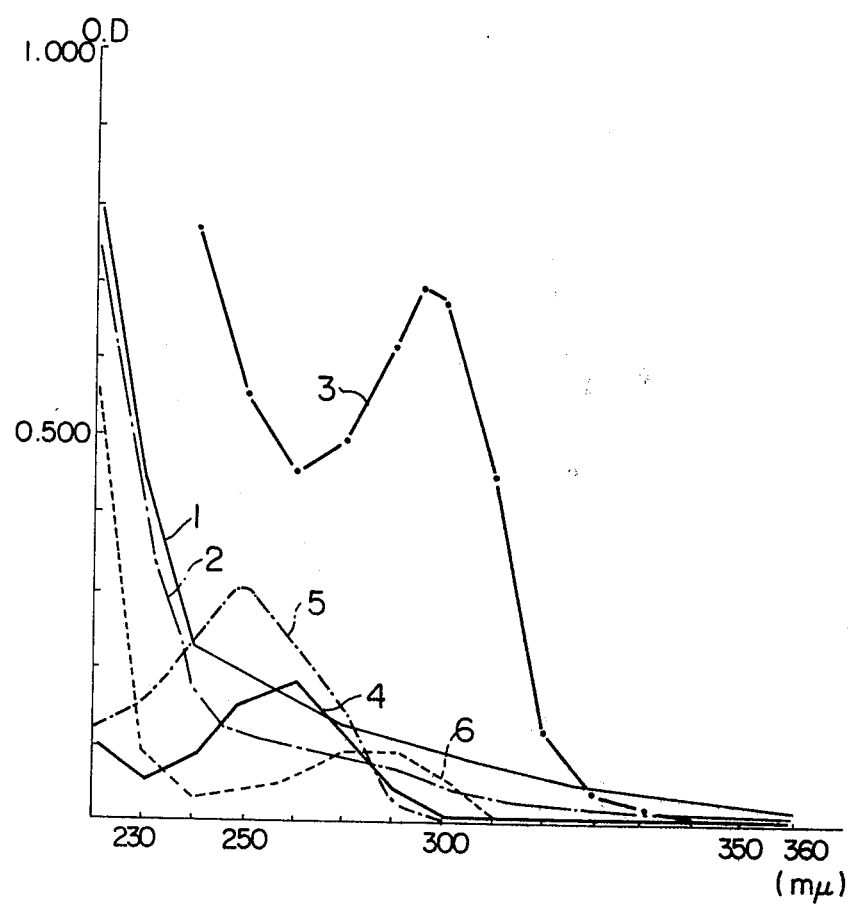
Figure 3:
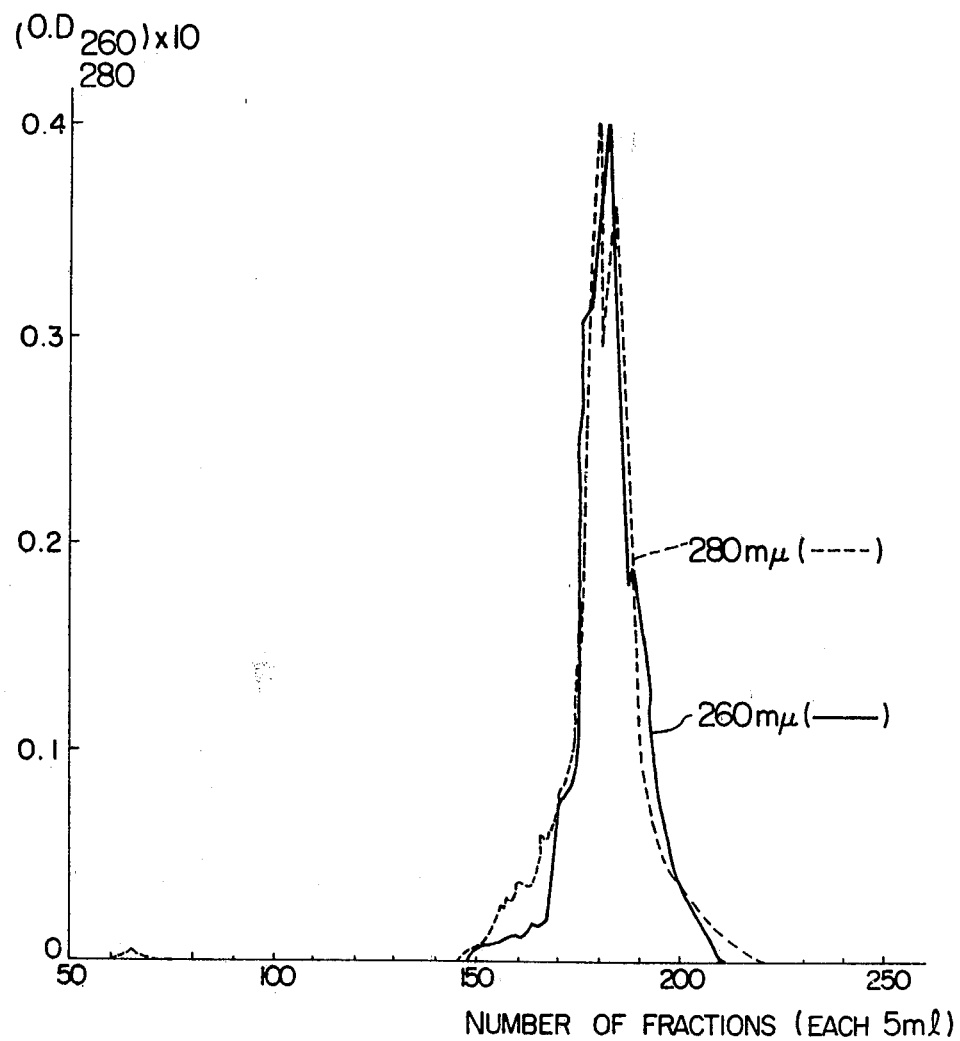
Figure 4:
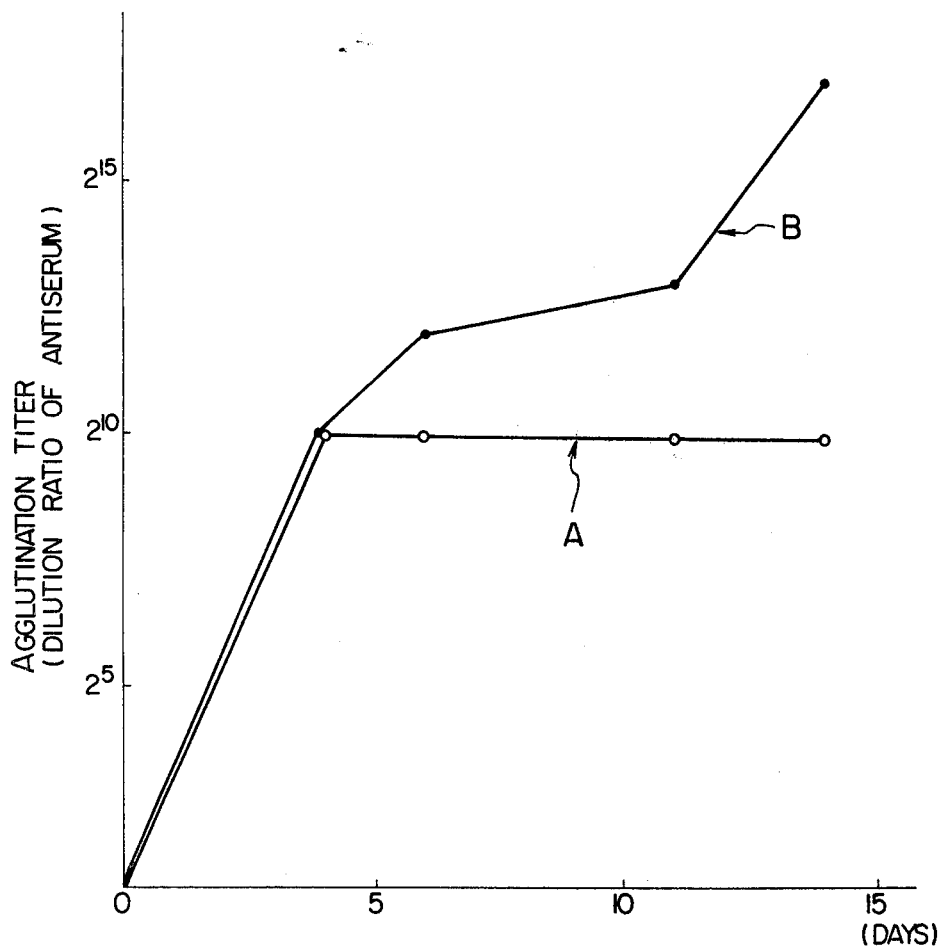
Figure 5:
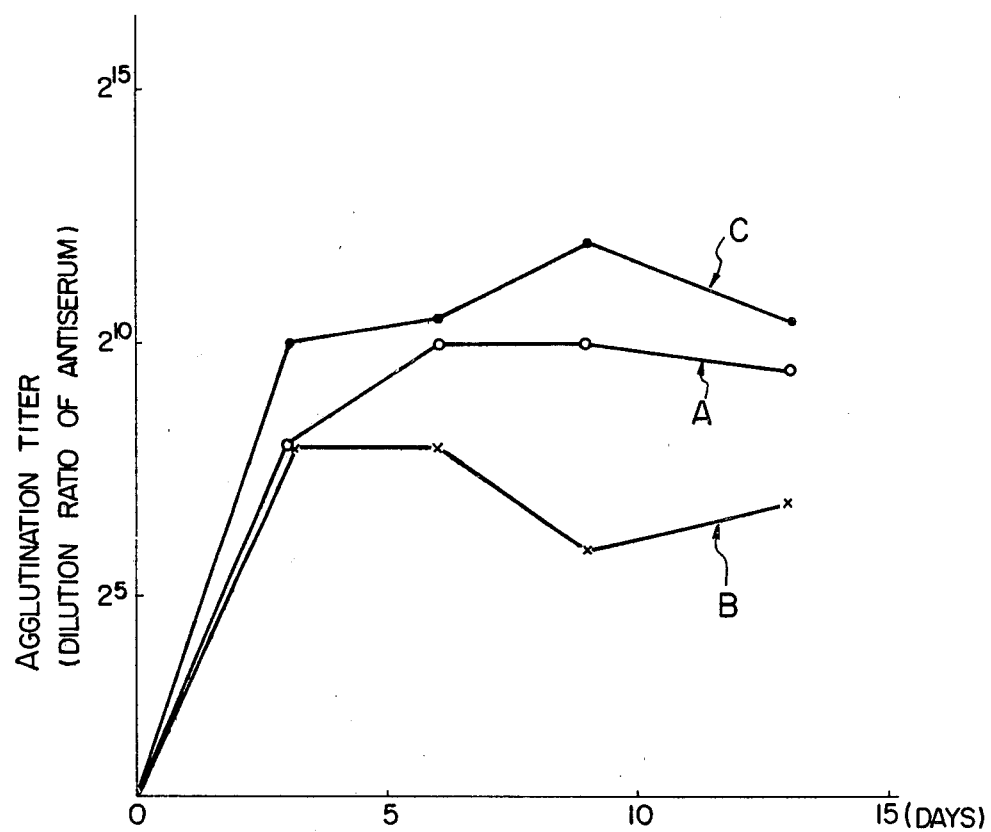
Figure 6:
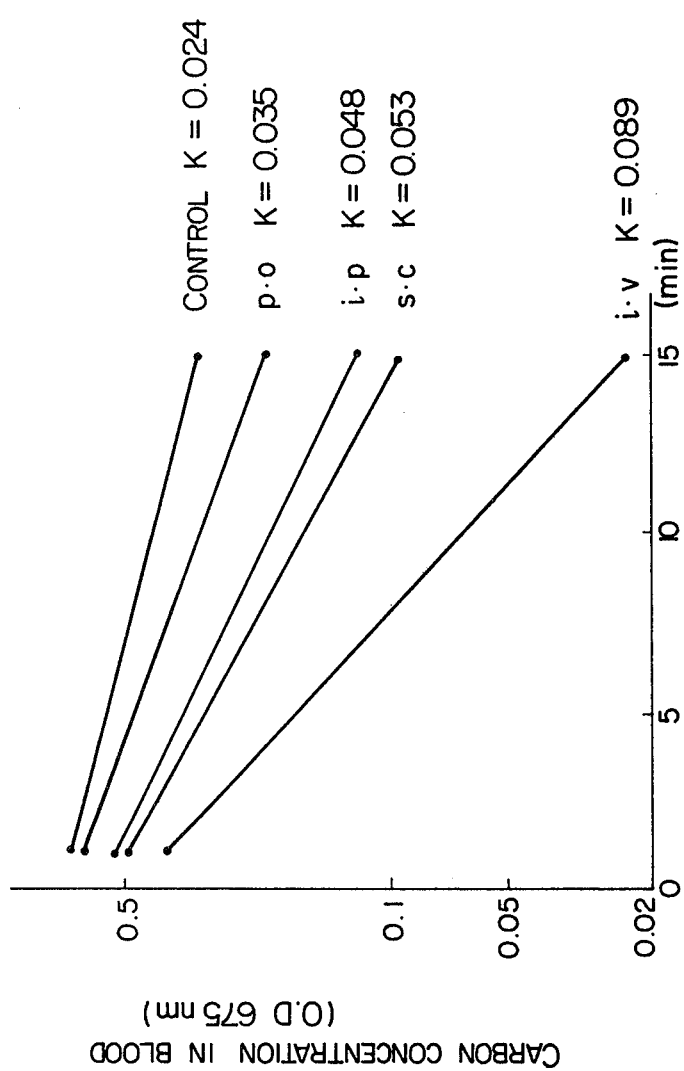

This invention is described in detail referring to the accompanying drawings, in which FIG. 1 shows an elution pattern where the B-T was subjected to gel filtration by means of Sephadex G-10; FIG. 2 shows an ultraviolet absorption sepctra of six fractions obtained by subjecting the B-T to gel filtration by means of Sephadex G-10; FIG. 3 shows an elution pattern where the B-T was subjected to gel filtration by means of Sephadex G-50; FIG. 4 shows the effect of the B-T on humoral immunity in normal mouse; FIG. 5 shows the effect of the B-T on humoral immunity in cancerous mouse; and FIG. 6 shows the effect of the B-T on the carbon clearance.

The B-T has already been known to be effective for treating neuralgia, rheumatism, stiff shoulder, lumbago, notalgia and myosalgia (New Drugs in Japan Vol. 4, 130), and is now clinically used as a drug for treating the above-mentioned diseases, but it is not known at all that the B-T has an immunostimulating activity, an effect of enhancing the carcinostatic activity of a carcinostatic substance or an effect of enhancing the antibacterial activity of an antibacterial substance.

The B-T can be obtained in the following manner. The poison pouch may be of any bee, though it is convenient to obtain a component obtained by deproteinizing an extract from the poison pouch contents of honeybees which can easily be obtained in a large amount throughout the year. A method of the extraction and deproteinization has already been known, and there is employed, for example, a method comprising extracting the poison pouch contents of bee with acidic distilled water having added thereto sodium chloride, heating the extract obtained to 50° to 100° C., removing the resulting precipitates, adding carbolic acid to the supernatant, and then filtering the resulting mixture (Japanese Patent Publication No. 991/54), or a usual treatment method comprising extracting the poison pouch contents of bee with warm water, and then deproteinizing the extract obtained.

The deproteinization treatment is carried out by usual methods alone or in combination, for example, a precipitation method by which an organic solvent such as acetone, an alcohol or the like or carbolic acid is added, a molecular sieving method, an ion exchange resin method, an ultracentrifugation method, a dialysis method, a method of precipitation at the isoelectric point, and the like.

An embodiment of the process for preparing the B-T is as follows: That is to say, first of all, the poison pouch of bee, preferably after pressing, is extracted with water or an aqueous sodium chloride solution. Specifically, it is preferable to add to the pouch water or an aqueous sodium chloride solution in an amount of about 0.025 ml per one poison pouch, and subject the resulting mixture to extraction at 5° C. for 5 to 7 days while shaking it several times a day.

Subsequently, the extract thus obtained is heated to 50° to 100° C., and the resulting precipitates are removed. Thereafter, deproteinization is carried out by (1) a method comprising adjusting the pH of the mother liquor to 3.8 to 5.0, removing the resulting precipitates by filtration, heating the filtrate to said temperature, removing the resulting precipitates by filtration, adding an ether to the filtrate to remove the ether-soluble fraction, or (2) a method comprising adding to the mother liquor water or an aqueous sodium chloride solution containing carbolic acid preferably in an amount of 1 to 5% by weight of the mother liquor, removing the resulting precipitates, adjusting the pH of the mother liquor to 5 to 7, heating it at about 50° to 100° C., freezing it at −5° to −30° C., thereafter melting it gradually, and then removing the resulting precipitates. The desired liquid substance can be obtained thereby.

It is also possible to obtain the desired powdery substance by freeze-drying the liquid substance as obtained or after desalting the same by a conventional method such as an ion-exchange resin method, a molecular sieving method or the like.

Although the details of the composition of the B-T are not yet clear, the B-T obtained in the manner described above has the following physical properties:
  (i) A colorless or slightly yellow transparent liquid.
  (ii) Negative in biuret reaction and sulfosalicylic acid reaction.
  (iii) It contains a very little or substantially no phospholipase A, hyaluronidase and mellitin
  (iv) When the B-T obtained, for example, by the above-mentioned method (2) is fractionated by gel filtration (column: 3.8×38 cm, eluent: distilled water) by means of Sephadex G-10 (a registered trademark of Pharmacia Co., Ltd.), six fractions having absorption at O.D. 260 mμ in ultraviolet absorbance measurement are obtained as shown in FIG. 1. All of the six fractions have ultraviolet absorptions as shown in FIG. 2.

(v) When the B-T obtained, for example, by the above-mentioned method (2) is subjected to gel filtration (column: 3.6×52 cm, eluent: distilled water) by means of Sephadex G-50 (a registered trademark of Pharmacia Co., Ltd.), the results are as shown in FIG. 3, and the fraction near the void volume and one of the other fractions show peaks.

(vi) A powder prepared by freeze-drying the desired liquid substance obtained by the above-mentioned method (2) has no antibacterial activity, as shown in Table 1.

TABLE 1

| Name of bacteria | Inoculated amount (cells/ml) | MIC (μg/ml) |
|---|---|---|
| St. aureus FDA 209 | 1 × 10$^4$ | >800 |
| E. coli NIHJ | 4.1 × 10$^4$ | >800 |
| E. coli TK-16 | 4.5 × 10$^4$ | >800 |

(Experimental Method)

Each of the test bacteria was inoculated at a population of 10$^4$ cells/ml on an ordinary medium containing a B-T freeze-dried product at each concentration, and was cultured at 37° C. for 18 hours, after which the turbidity was judged with the naked eye. The concentration of the drug at which no turbidity was observed was defined as a minimum inhibitory concentration (MIC).

The pharmacological effects of the B-T are shown below. As the B-T, the component obtained in Production Example 1 which appears hereinafter was used.

The liquid product obtained in Production Example 1-(1) is referred to as B-TL, the B-TL diluted to five volumes with a physiological salt solution as B-TL 1/5, the B-TL diluted to ten volumes therewith as B-TL 1/10, the B-TL diluted to 100 volumes therewith as B-TL 1/100, and the freeze-dried product obtained in Production Example 1-(2) as B-TP.

I. Immunostimulating activity (1) Humoral immunity-stimulating effect in normal mouse Sheep erythrocytes were washed twice with a phosphate buffer solution (0.01 M phosphate buffer containing 0.85% of sodium chloride and having a pH of 7.2), and the erythrocyte population thereof was adjusted to 5×10$^8$ cells/ml (the suspension thus obtained is hereinafter referred to as an antigen suspension), and the antigen suspension was then administered to a group of five ICR-strain mice (female, 5 to 6 weeks old), through the vein of the tail to perform antigen sensitization. B-TL 1/10 was administered subcutaneously at a dosage of 0.25 ml per mouse a day repeatedly for 7 days from the antigen sensitization day. A mouse serum was taken on the 4th, 6th, 8th, 12th and 15th days after the antigen sensitization, and diluted solutions (each 2 ml) of the serum with the above buffer solution in a two-volume dilution series were prepared. To each of the solutions was added 0.2 ml of the aforesaid antigen suspension, and the resulting mixture was allowed to stand overnight at 4° C., after which the presence or absence of agglutination was judged, and the minimum dilution ratio at which agglutination took place was determined and defined as agglutination titer.

The results are as shown in FIG. 4, wherein curve A shows the agglutination titer of normal mouse and curve B shows that of a mouse to which B-TL 1/10 was administered. As is obvious from FIG. 4, the agglutination titer showed a constant value in the case of the group to which no B-T was administered, while in the case of the group to which the B-T was administered, the agglutination titer was increased and the humoral immunity of normal mouse was increased.

(2) Humoral immunity-stimulating effect in cancerous mouse

Sheep erythrocytes were washed twice with a phosphate buffer solution (0.01 M phosphate buffer containing 0.85% by weight of sodium chloride and having a pH of 7.2), and the number of erythrocytes was adjusted to 5×10$^8$ cells/ml (the suspension thus obtained is hereinafter referred to as an antigen suspension), and the suspension was then administered to ICR-strain mice (female, 5 to 6 weeks old) through the vein of the tail to perform antigen sensitization. Two hours after the atnigen sensitization, Ehrlich's ascites tumor cells were transplanted intraperitoneally in an amount of 1×10$^5$ cells/mouse. B-TL 1/10 was administered to each mouse subcutaneously at the back at a dosage of 0.25 ml once a day for 7 days from the day of tumor cells-transplantation to the sixth day. A mouse serum was taken on the 3rd, 6th, 9th and 13th days after the antigen sensitization, and diluted solutions (each 0.2 ml) of the serum with the above buffer solution in a two-volume dilution series were prepared. To each of the diluted solutions was added 0.2 ml of the aforesaid antigen suspension, and the resulting mixture was allowed to stand overnight at 4° C., after which the presence or absence of agglutination was judged, and the minimum dilution ratio at which agglutination took place was determined and defined as agglutination titer.

The results are as shown in FIG. 5, wherein curve A shows the agglutination titer of the normal mouse, curve B shows that of the concerous mouse, and curve C shows that of the cancerous mouse to which B-TL 1/10 was administered.

As is obvious from FIG. 5, the agglutination titer of the normal mouse shows a constant value, while the agglutination titer of the cancerous mouse is 1/16 to ¼ of that of the normal mouse. When the B-T was administered to the cancerous mouse, the agglutination titer is higher than the agglutination titer of the normal mouse, and the humoral immunity was increased.

(3) Cellular immunity-stimulating effect evaluated by a carbon clearance method

B-TP was administered at a dosage of 20 mg/kg per mouse to a group of mice subcutaneously at the back, to another group of mice intraperitoneally, to a further group of mice intravenously and to another group of mice orally. Twenty-four hours after the administration, a carbon suspension prepared by mixing 1 ml of Perikan Drawing Ink 17 Black (manufactured by Cünter-Wagner Co., Ltd.) with 2 ml of a physiological salt solution containing 3% by weight of gelatin was injected in an amount of 0.2 ml into each of the mice through the vein of the tail, and 1, 5, 10 and 15 minutes which the B-T was administered together with Mitomycin C, a remarkable life-prolonging effect was observed as compared with the group to which Mitomycin C was administered alone, and the survival rate was high. Therefore, the carcinostatic activity-enhancing effect of the B-T was confirmed. The same tendency was confirmed also in the case of the inoculation of $1 \times 10^4$ and $1 \times 10^5$ cells of L-1210 leukemia.

(2) In the same manner as in (1), L-1210 leukemia cells were inoculated and MMC and the B-T were administered. B-TL 1/10 was administered subcutaneously at the back, at the breast or at the neck at a dose of 0.1 ml per mouse three times on the day of inoculation, twice on the first and second days after the inoculation, and once on the third, 4th, 5th and 6th days after the inoculation.

The results are as shown in Table 5.

TABLE 5

| Number of L-1210 leukemia cells inoculated | Dose of MMC | Dose of B-TL 1/10 | T/C (%) | Number of survivors Number of tested mice (on the 40th day) |
|---|---|---|---|---|
| $1 \times 10^3$ cells/mouse | — | — | 100 | 0/4 |
| $1 \times 10^3$ cells/mouse | 4 mg/kg | — | 187 | 1/4 |
| $1 \times 10^3$ cells/mouse | 4 mg/kg | 0.3–0.9 ml × 3 × 7 | 304 | 3/4 |
| $1 \times 10^4$ cells/mouse | — | — | 100 | 0/4 |
| $1 \times 10^4$ cells/mouse | 4 mg/kg | — | 202 | 1/4 |
| $1 \times 10^4$ cells/mouse | 4 mg/kg | 0.3–0.9 ml × 3 × 7 | 259 | 1/4 |
| $1 \times 10^5$ cells/mouse | — | — | 100 | 0/4 |
| $1 \times 10^5$ cells/mouse | 4 mg/kg | — | 136 | 0/4 |
| $1 \times 10^5$ cells/mouse | 4 mg/kg | 0.3–0.9 ml × 3 × 7 | 321 | 3/4 |

As is clear from Table 5, when curative effects in the case of the inoculation of $1 \times 10^3$, $1 \times 10^4$ and $1 \times 10^5$ cells of L-1210 leukemia are compared, the groups to which the B-T was administered together with Mitomycin C were superior in life-prolonging rate (T/C) and survival rate to the groups to which Mitomycin C was administered alone, and the carcinostatic activity-enhancing effect of the B-T was confirmed.

(3) L-1210 leukemia cells were inoculated intraperitoneally into BDF$_1$-strain mice (male, 6 to 7 weeks old) in an amount of $1 \times 10^3$ cells per mouse, and B-TL 1/10 was administered subcutaneously at the back at a dose of 0.25 ml per mouse once a day repeatedly from the day of inoculation for 7 days in total. Arabinofuranocylcytocine (Ara-C) was administered intraperitoneally at a dose of 30 mg/kg once a day from the day following the inoculation of the cancerous cells for 5 days in total.

The results are as shown in Table 6.

TABLE 6

| Dose of Ara-C | Dose of B-TL 1/10 | T/C (%) | Number of survivors Nubmer of tested mice (on the 30th day) |
|---|---|---|---|
| — | — | 100 | 0/4 |
| 30 mg/kg × 5 | — | 152 | 0/4 |
| 30 mg/kg × 5 | 0.25 ml × 7 | 198 | 1/4 |

As is clear from Table 6, the group to which B-T was administered together with Arabinofuranocylcytocine showed remarkable enhancement of a carcinostatic activity of Arabinofuranocylcytocine as compared with the group to which Arabinofuranocylcytocine was administered alone.

(4) L-1210 leukemia cells were inoculated subcutaneously at the armpit of BDF$_1$-strain mice (male, 7 weeks old) in an amount of $1 \times 10^6$ cells per mouse to form a tuberous tumor. B-TL 1/10 was administered subcutaneously at the back at a dose of 0.25 ml per mouse once a day repeatedly from the first day after the inoculation of the cancerous cells for 7 days in total, and Mitomycin C was administered into the tumor at a dose of 4 mg/kg on the first day after the inoculation of the cancerous cells.

The result are as shown in Table 7.

TABLE 7

| Dose of MMC | Dose of B-TL 1/10 | T/C (%) | Number of survivors Number of tested mice (on the 30th day) | Weight of tumor* mg | Ratio to Control |
|---|---|---|---|---|---|
| — | — | 100 | 0/5 | 517 ± 144 (on the 8–10th day) | 100 |
| 4 mg/kg | — | 304 | 4/5 | 808 ± 461 (on the 30th day) | 156 |
| 4 mg/kg | 0.25 ml × 7 | 304 | 4/5 | 103 ± 131 (on the 30th day) | 20 |

*Since all the mice in the control group (untreated group) died on the 8th to 10th day, the weights of the tumors at the time of death were measured in this case. In the case of the group to which Mitomycin C was administered alone and the group to which the B-T was administered together with Mitomycin C, the weights of tumors of 4 survivors among the 5 tested mice were measured on the 30th day.

As is clear from Table 7, the weights of tumors was remarkably smaller in the case of the group to which the B-T was administered together with Mitomycin C than in the case of the group to which Mitomycin C was administered alone, and an clear effect of inhibiting the growth of the tumors was confirmed.

2. Effect of enhancing carcinostatic activity of Mitomycin C to P-388 leukemia cells P-388 leukemia cells were inoculated intraperitoneally into BDF$_1$-strain mice (male, 7 weeks old) in an amount of $1 \times 10^3$ cells per mouse, and B-TL 1/10 was administered subcutaneously at the back at a dose of 0.25 ml per mouse on the day of inoculation and thereafter administered subcutaneously at the back at the same dose once a day repeatedly for 7 days. Mitomycin C (MMC) was administered intraperitoneally at a dose of 0.5 mg/kg on the first day after the inoculation of the P-388 leukemia cells.

The results are as shown in Table 8.

after the injection, 0.02 ml of the blood was sampled from the eyehole of each mouse by means of a Hematocrit capillary tube coated with heparin, immediately diluted and hemolyzed with 1.6 ml of 0.1% by weight aqueous sodium carbonate, and then subjected to colorimetry at a wavelength of 675 nm. The phagocytic index, K value, was determined according to the mathematics of Helpern et al. from the equation $$K = \frac{\log C_0 - \log C}{t - t_0}$$

wherein $C_0$ is the carbon amount in blood at time $t_0$ and C is the carbon amount in blood at time t.

The results are as shown in FIG. 6.

As is obvious from FIG. 6, the K values are 0.024 for the group to which the B-T was not administered (control), 0.035 for the group to which the B-T was orally administered (p.o.), 0.048 for the group to which the B-T was administered intraperitoneally (i.p.), 0.053 for the group to which B-T was administered subcutaneously at the back (s.c.), and 0.089 for the group to which the B-T was intraveneously administered (i.v.). The B-T administration activated the reticuloendothelial macrophages and increased the cellular immunity of the normal mouse.

II. Carcinostatic activity (1) Carcinostatic activity to Ehrlich's ascites tumor Ehrlich's ascites cancerous cells were intraperitoneally inoculated into ICR-strain mice (female, 6 weeks old) in an amount of $1 \times 10^6$ cells per mouse. B-TL 1/10 was administered intraperitoneally, subcutaneously at the back or intravenously at a dose of 0.25 ml per mouse once a day repeatedly for 7 days from 7 days before the inoculation of the cancer cells (Experiment 1), or once a day for 7 days from one day after the inoculation of the cancer cells (Experiment 2).

$$T/C = \frac{\text{Number of survival days of administration group}}{\text{Number of survival days of control group}} \times 100\ (\%)$$

The results are as shown in Table 2.

TABLE 2

| Exper. No. | Dose of B-TL 1/10 | Administration site | TIC (%) | Number of survivors / Number of tested mice (on the 30th day) |
|---|---|---|---|---|
| 1 | — | | 100 | 0/3 |
| | 0.25 ml × 7 | Intraperitoneally | 104 | 0/3 |
| | 0.25 ml × 7 | Subcutaneously at the back | 125 | 0/3 |
| | 0.25 ml × 7 | Intravenously | 110 | 0/3 |
| 2 | — | | 100 | 0/3 |
| | 0.25 ml × 7 | Intraperitoneally | 132 | 0/3 |
| | 0.25 ml × 7 | Subcutaneously at the back | 113 | 0/3 |
| | 0.25 ml × 7 | Intravenously | 120 | 0/3 |

As is clear from Table 2, a life-prolonging effect is observed when the B-T is administered.

(2) Carcinostatic activity to Sarcoma-180 ascites tumor

Sarcoma-180 cancerous cells were inoculated intraperitoneally into ICR-strain mice (female, 6 weeks old) in an amount of $5 \times 10^6$ cells per mouse.

B-TL, B-TL 1/10, and B-TL 1/100 were administered intraperitoneally at a dose of 0.25 ml per mouse once a day repeatedly from the third day after the inoculation of the cancerous cells for 5 days, namely five times in total.

The results are as shown in Table 3.

TABLE 3

| | Dose of B-T | T/C (%) | Number of survivors / Number of tested mice (on the 27th day) |
|---|---|---|---|
| | — | 100 | 0/5 |
| B-TL | 0.25 ml × 5 | 142 | 0/4 |
| B-TL 1/10 | 0.25 ml × 5 | 118 | 0/4 |
| B-TL 1/100 | 0.25 ml × 5 | 129 | 0/4 |

As is clear from Table 3, a life-prolonging effect is observed when the B-T is administered.

III. Effect of enhancing carcinostatic activity of a carcinostatic substance

1. Effect of enhancing carcinostatic activity of Mitomycin C to L-1210 leukemia cells (1) L-1210 leukemia cells were inoculated intraperitoneally into BDF$_1$-strain mice (male, 6 to 7 weeks old) in an amount of $1 \times 10^3$, $1 \times 10^4$ or $1 \times 10^5$ cells per mouse, B-TL 1/10 was administered subcutaneously at the back at a dose of 0.25 ml per mouse once a day repeatedly from the day of inoculation for 7 days in total. Mitomycin C (MMC) was administered intraperitoneally at a dose of 4 mg/kg on the first day after the inoculation of the cancerous cells.

The results are as shown in Table 4.

TABLE 4

| Number of L-1210 leukenia cells inoculated | Dose of MMC | Dose of B-TL 1/10 | T/C (%) | Number of survivors / Number of tested mice (on the 38th day) |
|---|---|---|---|---|
| $1 \times 10^3$ cells/mouse | — | — | 100 | 0/13 |
| $1 \times 10^3$ cells/mouse | 4 mg/kg | — | 192 | 4/13 |
| $1 \times 10^3$ cells/mouse | 4 mg/kg | 0.25 ml × 7 | 269 | 9/13 |
| $1 \times 10^4$ cells/mouse | — | — | 100 | 0/9 |
| $1 \times 10^4$ cells/mouse | 4 mg/kg | — | 188 | 2/9 |
| $1 \times 10^4$ cells/mouse | 4 mg/kg | 0.25 ml × 7 | 261 | 4/9 |
| $1 \times 10^5$ cells/mouse | — | — | 100 | 0/4 |
| $1 \times 10^5$ cells/mouse | 4 mg/kg | — | 136 | 0/4 |
| $1 \times 10^5$ cells/mouse | 4 mg/kg | 0.25 ml × 7 | 238 | 1/4 |

As is clear from Table 4, all the mice in the group to which no drug was administered died on 12th to 15th day when $1 \times 10^3$ L-1210 leukemia cells were inoculated. On the other hand, a life-prolonging effect was observed in the case of the group to which Mitomycin C was administered, and in the case of the group to

TABLE 8

| Dose of MMC | Dose of B-TL 1/10 | T/C (%) | Number of survivors / Number of tested mice (on the 41st day) |
|---|---|---|---|
| — | — | 100 | 0/4 |
| 0.5 mg/kg | — | 101 | 0/3 |
| 0.5 mg/kg | 0.25 ml × 7 | 155 | 1/3 |

As is clear from Table 8, the group to which the B-T was administered together with Mitomycin C showed a remarkable enhancement of the carcinostatic activity of Mitomycin C, as compared with the group to which Mitomycin C was administered alone.

3. Effect of enhancing a carcinostatic activity of Mitomycin C to Ehrlich's ascites cancer cells (1) Ehrlich's ascites cancer cells were inoculated intraperitoneally into ICR-strain mice (female, 6 weeks old) in an amount of 1×10⁵ cells per mouse, and B-TL 1/10 was administered subcutaneously at the back at a dose of 0.25 ml per mouse once a day repeatedly from the third day after the inoculation of the cancerous cells for 7 days in total. Mitomycin C (MMC) was administered intraperitoneally at a dose of 0.5 mg/kg on the first day after the inoculation of the cancerous cells.

The results are as shown in Table 9.

TABLE 9

| Dose of MMC | Dose of B-TL 1/10 | T/C (%) | Number of survivors / Number of tested mice (on the 40th day) |
|---|---|---|---|
| — | — | 100 | 0/10 |
| 0.5 mg/kg | — | 158 | 1/10 |
| 0.25 mg/kg | 0.25 ml × 7 | 208 | 5/10 |

As is clear from Table 9, the group to which the B-T was administered together with Mitomycin C showed a remarkable enhancement of the carcinostatic activity of Mitomycin C as compared with the group to which Mitomycin C was administered alone.

(2) Ehrlich's ascites cancerous cells were inoculated intraperitoneally into ICR-strain mice (male, 6 weeks old) in an amount of 1×10⁵ cells per mouse. B-TL 1/10 was administered subcutaneously at the back at a dose of 0.25 ml per mouse once a day repeatedly from the day of inoculation for 7 days in total. On the day following the inoculation of the cancerous cells, 0.25 mg/kg of Carboquan (CQ) or 5 mg/kg of Adriamycin (AM) was administered intraperitoneally.

The results are as shown in Table 10.

TABLE 10

| Dose of a carcinostatic substance | Dose of B-TL 1/10 | T/C (%) | Number of survivors / Number of tested mice (on the 40th day) |
|---|---|---|---|
| — | — | 100 | 0/4 |
| CQ | — | 138 | 0/4 |
| 0.25 mg/kg | 0.25 ml × 7 | 149 | 2/4 |
| AM | — | 175 | 2/4 |
| 5 mg/kg | 0.25 ml × 7 | 192 | 3/4 |

As is clear from Table 10, the groups to which the B-T was administered together with Carboquan or Adriamycin showed a remarkable enhancement of the carcinostatic activity of Carboquan or Adriamycin, as compared with the groups to which Carboquan or Adriamycin was administered alone.

(3) B-TL 1/10 was administered subcutaneously at the back of ICR-strain mice (male, 5 weeks old) at a dose of 0.25 ml per mouse once a day repeatedly for 8 days in total, and on the day following the eighth administration, 1×10⁵ Ehrlich's ascites cancerous cells were inoculated intraperitoneally. On the day following the inoculation of the cancerous cells, Mitomycin C (MMC) was administered intraperitoneally at a dose of 0.5 mg/kg or 1 mg/kg.

The results are as shown in Table 11.

TABLE 11

| Dose of MMC | Dose of B-TL 1/10 | T/C (%) | Number of survivors / Number of tested mice (on the 40th day) |
|---|---|---|---|
| — | — | 100 | 0/5 |
| 0.5 mg/kg | — | 157 | 1/5 |
|  | 0.25 ml × 8 | 182 | 2/5 |
| 1 mg/kg | — | 172 | 0/5 |
|  | 0.25 ml × 8 | 187 | 2/5 |

As is clear from Table 11, the group to which the B-T was administered together with Mitomycin C showed a remarkable enhancement of the carcinostatic activity of Mitomycin C as compared with the group to which Mitomycin C was administered alone. Two survivors in the group to which the B-T was administered together with 1 mg/kg of Mitomycin C were normal.

4. Effect of enhancing carcinostatic activity of Adriamycin to B-16 melanoma cancerous cells Fifteen grams of B-16 melanoma cell cluster was milled by means of a mesh, and then suspended in 15 ml of a physiological salt solution, after which the resulting suspension was transplanted intraperitoneally in BDF₁-strain mice (male, 6 weeks old) in an amount of 0.2 ml per mouse (i.e., 0.2 g of the cells were transplanted per mouse). B-TL 1/10 was administered subcutaneously at the back at a dose of 0.25 ml per mouse once a day for 7 days from the day of transplantation. Adriamycin (AM) was administered intraperitoneally once at a dose of 2 mg/kg on the day following the day of cancer transplantation.

The results are as shown in Table 12.

TABLE 12

| Dose of AM | Dose of B-TL 1/10 | T/C (%) | Number of survivors / Number of tested mice (on the 35th day) |
|---|---|---|---|
| — | — | 100 | 0/4 |
| 2 mg/kg | — | 182 | 1/4 |
| 2 mg/kg | 0.25 ml × 7 | 208 | 4/4 |

As is clear from Table 12, the group to which the B-T was administered with Adriamycin showed an effect of enhancing a carcinostatic activity of Adriamycin as compared with the group to which Adriamycin was administered alone. The reason why the difference in T/C between the two groups is small is that the judgement was made on the 35th day. All the survivors in the group to which the B-T was administered together with Adriamycin were normal mice in which the tumor was completely cured.

IV. Effect of enhancing antibacterial activity of an antibacterial substance 1. Infection-controlling effect against *Escherichia coli*

(1) *Escherichia coli* TK-16 was inoculated intraperitoneally into groups of fifteen ICR mice (male, 4 weeks old) in an amount as shown in Table 13. B-TL 1/5 was administered at a dose of 0.25 ml per mouse once a day on the 7th, 6th and 5th days before the inoculation of the bacteria, and B-TL 1/10 was administered subcutaneously at the back at a dose of 0.25 ml per mouse once a day on the second and first days before the day of inoculation. A physiological salt solution was administered to the control group in the same manner as described above, and numbers of the survivors on the 7th day after the inoculation of the bacteria was observed. The results are as shown in Table 13.

TABLE 13

| Number of bacteria inoculated (cells/mouse) | Bacteria number ratio | Control | | Groups to which B-T was administered | |
|---|---|---|---|---|---|
| | | Number of survivors | Survival rate | Number of survivors | Survival rate |
| $2.5 \times 10^6$ | 5 | 1 | 6.7 | 12 | 80 |
| $1.25 \times 10^6$ | 2.5 | 7 | 46.6 | 14 | 93.3 |
| $1.0 \times 10^6$ | 2 | 8 | 53.3 | 15 | 100 |
| $5.0 \times 10^5$ | 1 | 9 | 60 | 15 | 100 |

As is clear from Table 13, the group to which the B-T was administered showed an infection-controlling effect as compared with the group to which no B-T was administered (control). This is thought to be because antiinfection immunity was stimulated by the administration of the B-T to exert an infection-controlling effect.

(2) *Escherichia coli* TK-16 was inoculated intraperitoneally into ICR-strain mice (male, 4 weeks old) in an amount as shown in Table 14. A solution of 3 mg of B-TP in 1 ml of a physiological salt solution was subcutaneously at the back or intravenously at the tail at a dose of 0.25 ml (0.75 mg in terms of B-TP) per mouse once a day on the 7th, 6th and 5th days before the inoculation of the bacteria, namely three times in total, and a solution of 1.5 mg of B-TP in 1 ml of a physiological salt solution was administered subcutaneously at the back or intravenously at the tail at a dose of 0.25 ml (0.38 mg in terms of B-TP) per mouse once a day on the second and first day before the inoculation of the bacteria, namely twice in total, and the number of the survivors on the 7th day after the inoculation of the bacteria was observed. A physiological salt solution was administered subcutaneously at the back of the mice in the control group in the same manner as described above. The results are as shown in Table 14.

TABLE 14

| Number of bacteria inoculated (cells/mouse) | Number of survivors/Number of tested mice | | |
|---|---|---|---|
| | Control | Groups to which B-T was administered | |
| | | Subcutaneously at the back | Intravenously at the tail |
| $6.9 \times 10^6$ | 0 | 2/5 | 5/5 |
| $4.6 \times 10^6$ | 0 | 3/5 | 5/5 |
| $3.5 \times 10^6$ | 2 | 3/5 | 5/5 |
| $2.3 \times 10^6$ | 3 | 4/5 | 5/5 |
| $1.2 \times 10^6$ | 3 | 4/5 | 5/5 |
| $6.0 \times 10^5$ | 5 | 5/5 | 5/5 |
| $3.5 \times 10^5$ | 5 | 5/5 | 5/5 |

As is clear from Table 14, the B-T had a remarkable infection-controlling effect in the cases of the intravenous administration and the subcutaneous administration of freeze-dried product, and had a great effect particularly in the case of the intravenous administration.

2. Infection-controlling effect on *Serratia marcescens*, *Pseudomonas areruginosa* and *Klebsiella pneumoniae*

A suspension of *S. marcescens* W-31, *Ps. aeruginosa* S-19 or *K. pneumoniae* Y-46 in an amount as shown in Table 15 in a physiological salt solution containing 5% by weight of mucin was administered intraperitoneally into a group of five ICR-strain mice (male, 4 weeks old). B-TL 1/5 was administered subcutaneously at the back at a dose of 0.25 ml per mouse once a day on the 7th, 6th and 5th days before the inoculation of the bacteria, and B-TL 1/10 was administered similarly at a dose of 0.25 ml per mouse once a day on the second and first days before the inoculation of the bacteria. A physiological salt solution was administered to the control group in the same manner as described above, and the numbers of the survivors on the 7th day after the inoculation of the bacteria were observed, and the minimum lethal dosage (MLD) was obtained.

The results are as shown in Table 15.

TABLE 15

| Name of bacteria | MLD (cells/mouse) | |
|---|---|---|
| | Control | Groups to which B-T was administered |
| *S. marcescens* W-31 | $10^7$ | $10^8$ |
| *Ps. aeruginosa* S-19 | $10^5$ | $10^7$ |
| *Kleb. pneumoniae* Y-46 | $10^7$ | $10^8$ |

As is clear from Table 15, the groups to which the B-T was administered showed an infection-controlling effect, as compared with the control group. This is thought to be because the antiinfection immunity was stimulated by the administration of the B-T to exhibit an infection-controlling effect.

3. Infection-controlling effect at a low immunity

Cyclophosphamide was administered intraperitoneally into a group of fifteen ICR-strain mice (male, 4 weeks old) at a dose of 100 mg/kg. On the next day, B-TL 1/10 was administered subcutaneously at the back at a dose of 0.25 ml per mouse once a day repeatedly for 4 days, and a physiological salt solution was administered to the control group in the same manner as described above. On the day following the administration of B-TL 1/10, *Escherichia coli* TK-16 was administered intraperitoneally, and the numbers of the survivors on the 7th day after the inoculation of the bacteria were observed.

The results are as shown in Table 16.

TABLE 16

| Number of bacteria inoculated (cells/mouse) | Control | Number of survivors Groups to which cyclophosphamide was administered | Groups to which cyclophosphamide and B-T was administered |
|---|---|---|---|
| $4.0 \times 10^6$ | — | — | 3 |
| $3.0 \times 10^6$ | 4 | — | 6 |
| $2.0 \times 10^6$ | 7 | — | 9 |
| $1.0 \times 10^6$ | 10 | 3 | 13 |
| $8.0 \times 10^5$ | 12 | 4 | 15 |
| $4.0 \times 10^5$ | 13 | 6 | — |
| $3.0 \times 10^5$ | — | 10 | — |
| $2.0 \times 10^5$ | — | 10 | — |
| $LD_{50}$ (cells/mouse) | $1.6 \times 10^6$ | $2.7 \times 10^5$ | $2.2 \times 10^6$ |

As is clear from Table 16, the $LD_{50}$ value is significantly lower in the case of the group to which cyclophosphamide was administered than in the case of the control, and the inhibition of the infection-controlling effect was confirmed. The $LD_{50}$ value of the group to which the B-T was administered together with cyclophosphamide is not different from that of the control, and the B-T recovered the infection-controlling effect inhibited by the administration of cyclophosphamide.

4. Antibacterial activity-enhancing effect of the B-T in *Escherichia coli*

*Escherichia coli* TK-16 was administered intraperitoneally into a group of five ICR-strain mice (male, 4 weeks old) in an amount of $2 \times 10^7$ cells/mouse, and after one hour, Piperacillin was administered once subcutaneously at the back. B-TL 1/5 was administered subcutaneously at the back at a dose of 0.25 ml per mouse once a day on the 7th, 6th and 5th days before the inoculation of the bacteria, and B-TL 1/10 at a dose of 0.25 ml per mouse once a day on the second and first days before the inoculation of the bacteria. A physiological salt solution was administered to the control group in the same manner as above, and the numbers of the survivors on the 7th day after the inoculation of the bacteria was observed.

The results are as shown in Table 17.

TABLE 17

| Dose of Piperacillin (mg/mouse) | Control | Number of survivors Groups to which B-T was administered |
|---|---|---|
| 2.5 | 2 | 5 |
| 1.25 | 0 | 4 |
| 0.625 | 1 | 3 |
| 0.313 | 0 | 2 |
| 0.156 | 0 | 2 |
| $ED_{50}$ (mg/mouse) | 3.54 | <0.38 |

As is clear from Table 17, the group to which the B-T was administered together with Piperacillin showed a significant curative effect, as compared with the control group, indicating the antibacterial activity-enhancing effect of the B-T.

As is clear from the above-mentioned experimental results of the pharmacological effects, the B-T has an immunostimulating activity, an effect of enhancing the carcinostatic activity of a carcinostatic substance, and an effect of enhancing the antibacterial activity of an antibacterial substance. The B-T is very low in toxicity, and the acute toxicity of B-TP in mouse is as shown in Table 18.

TABLE 18

| Administration method | $LD_{50}$ |
|---|---|
| Intravenously | >2 g/kg |
| Intramuscularly | >2 g/kg |
| Subcutaneously | >4 g/kg |

Therefore, the B-T can be used, in the medical field, as an immunostimulating agent.

Further, it can be used together with a carcinostatic substance or an antibacterial substance, as a carcinostatic agent or an antibacterial agent, respectively.

That is to say, the B-T is used, by utilizing its immunostimulating activity, for curing various diseases of infants and the aged who are low in immunity; for medical treatment when the immunity is decreased by radiotherapy, the administration of drugs or various diseases; and for enhancing the power of resistance to diseases caused by the decrease in immunity, for example, bacterial infection called opportunitic infection which brings about a serious condition of a patient. Furthermore, it can be used, by utilizing its effect of enhancing the carcinostatic activity of a carcinostatic substance or its effect of enhancing the antibacterial activity of an antibacterial substance, for treating the corresponding diseases by administering it together with a carcinostatic substance or an antibacterial substance, or by mixing it with these substances.

The B-T may be used either in liquid form as such or in solid or powder form prepared by freeze-drying or the like.

The B-T of this invention may be used together or mixed with any carcinostatic substance or antibacterial substance. As the carcinostatic substance, there may be exemplified, for example, alkylating agents such as Endoxan, Carboquan, and the like; antimetabolites such as 6-mercaptopurine, 5-fluorouracil, 1-(2-tetrahydrofuryl)-5-flurorouracil, and the like; carcinostatic antibiotics such as Mitomycin C, Bleomycin, Adriamycin, Daunomycin, and the like; vegetable mitotic toxins such as Vinblastine, Vincristine, and the like; bacteriocides such as BCG, BCG-CWS, asparaginase, OK-432, and the like; immunotherapeutical agents such as PSK, Maruyama vaccine, rencinan, and the like.

As the antibacterial substance, there may be exemplified β-lactam type antibiotics, for example, penicillin type antibiotics such as Ampicillin, Amoxycillin, Piperacillin, Carbenicillin, Dicloxacillin, Cyclacillin, Sulbenicillin, Hetacillin, Propicillin, Flucloxacillin, Cloxacillin, Oxacillin, and the like, cephalosporin type antibiotics such as Cephalexin, Cefoperazone (7-[D(-)-α-(4-ethyl-2,3-dioxo-1-piperazinylcarbonylamino)-p-hydroxyphenylacetamido]-3-[5-(1-methyl-1,2,3,4-tetrazolyl)thiomethyl]-$\Delta^3$-cephem-4-carboxylic acid), Cephalothin, Cephaloridine, Cephapirin, Cefradine, Cefazolin, Cephaloglycin and the like, and other β-lactam type antibiotics such as Tienamycin, (6R, 7R)-7-[2-carboxy-2-(4-hydroxyphenyl)acetamido]-7-methoxy-3-[(1-methyl-1H-tetrazol-5-yl-thio)methyl]-8-oxo-5-oxa-1-azabicyclo[4,2,0]oct-2-ene-2-carboxylic acid, (6R,7R)-7-[2-methoxyimino-2-(2-imino-4-thiazolin-4-yl)acetamido-8-oxo-5-thia-1-azabicylo[4,2,0]oct-2-ene-2-carboxylic acid, and the like; maclolide antibiotics such as Midecamycin, Josamycin, Acetylspiramycin, Erythromycin, Oleandomycin, Kitasamycin, Spiramycin, and the like; tetracycline type antibiotics such as Minocycline, Doxycycline, Methacycline, Tetracycline, Chlortetracycline, Oxytetracycline, Demethylchlortetracycline, Prolinomethyltetracycline, and the like; aminoglycoside type antibiotics such as Bistamycin, Lividomycin, Kanendomycin, Gentamicin, Baromomycin, Aminocidine, Kanamycin, Fradiomycin, Neomycin, and the like; polypeptide antibiotics such as Enduracidine, Capreomycin, Viomycin, Polymyxin B, Colistin, Bacitracin, Gramicidin, and the like; polyene antibiotics such as Bariothin, Amphotericin B, Trichomycin, Pentamycin, Pimaricin, Nystatin, and the like; antibiotics such as Liphamycin, Lincomycin, and the like; antibacterial substances such as nalidixymic acid, piromidic acid, and the like.

The B-T can be shaped into various drug forms such as oral drugs, injections, suppositories, and the like. Particularly, when it is mixed with a carcinostatic substance and an antibacterial substance, it may be shaped into the same forms as the drug forms of these substances. Depending upon the kind of the drug form, an antiseptic such as carbolic acid or the like may be added.

When shaped into an oral drug, it may contain various excipients, and may be shaped into capsules, tablets, powders and granules. When formed into an injection, it may be any of subcutaneous injections, intramuscular injections and intravenous injections, and may be used in such a form as suspension, solution, powder which is dissolved when used, or the like. The injections may contain a local anesthetic.

The administration methods and the dosages of the B-T, the carcinostatic substance, and the antibacterial substance of this invention is properly selected depending upon the properties of the carcinostatic substance and the antibacterial substance and upon the condition of a patient. As to the administration method, it is generally preferable to administer them alone or in the form of a compound drug orally, subcutaneously, intramuscularly, intravenously, or inject them into the affected part. The dosage in terms of the B-T may vary depending upon the purpose and the condition of a patient, though in usual, it is preferable to administer the B-T in a dose of 1 to 200 mg in terms of its freeze-dried product per kilogram per adult one to several times a day.

This invention is further explained below referring to Examples, which are merely by way of illustration and not by way of limitation.

PRODUCTION EXAMPLE 1

(1) In a mortar were placed 1,000 poison pouches of honeybee, and their contents were pressed out, after which 25 ml of a sterilized 0.8% by weight aqueous sodium chloride solution was added to the mortar. The resulting mixture was allowed to stand at 5° C. for 5 days while lightly shaking it several times a day. The precipitates were removed by filtration, and the filtrate was heated at 60° C. for 30 minutes, and then allowed to stand at 5° C. for 3 days while lightly shaking once a day. Subsequently, the resulting precipitates were removed by filtration, and 4 ml of a sterilized physiological salt solution containing 20% by weight of carbolic acid was added to the filtrate, after which the resulting mixture was allowed to stand at 5° C. for 7 days while lightly shaking it once a day. The resulting precipitates were removed by filtration, and the pH of the filtrate obtained was adjusted to 6.0 and the filtrate was then heated at 60° C. for 30 minutes. Subsequently, the filtrate was frozen at −5° to −10° C., and then allowed to stand for 3 to 5 days. The frozen filtrate was allowed to stand at room temperature to be gradually melted, and then filtered to obtain 26.3 ml of a slightly yellow liquid.

The above-mentioned procedures were carried out under sterile conditions.

(2) Fifteen milliliters of the deproteinized extract obtained in (1) was evaporated to dryness under reduced pressure under freezing to obtain 250 mg of a slightly yellow powder containing 47% of sodium chloride.

PRODUCTION EXAMPLE 2

In a mortar were placed 1,000 poison pouches of honeybee, and their contents were pressed out, after which 25 ml of a sterilized 0.9% by weight aqueous sodium chloride solution was added to the contents, and the resulting mixture was allowed to stand at 5° C. for 5 days while lightly shaking it several times a day. The resulting precipitates were removed by filtration, and the filtrate was heated at 60° C. for 30 minutes, and then allowed to stand at 5° C. for 3 days while lightly shaking once a day. Subsequently, the resulting precipitates were removed by filtration, after which 20 ml of diethyl ether was added to the filtrate, and the mixture thus obtained was sufficiently shaken. The ether layer was removed to obtain 43 ml of a slightly yellow liquid.

The above-mentioned procedures were carried out under sterile conditions.

PRODUCTION EXAMPLE 3

Thousand poison pouches of honeybee were taken out, and to the contents thereof was added 100 ml of sterilized 0.7% by weight aqueous sodium chloride solution adjusted to pH 6.0 with diluted hydrochloric acid, after which the mixture was subjected to extraction at 5° C. for 7 days, after which the supernatant solution was heated to 80° C., and the resulting precipitates were removed by centrifugal precipitation by means of a high-speed centrifuge at 12,000 revolutions per minute. Thereafter, to the mother liquor was added carbolic acid in an amount of 1/100 of the volume of the mother liquor, and the resulting precipitates were removed by filtration, after which the pH of the filtrate was adjusted to 6 to obtain 93 ml of a slightly yellow liquid.

The above-mentioned procedures were carried out under sterile conditions.

PRODUCTION EXAMPLE 4

In a mortar were placed 1,000 poison pouches of honeybee, and their contents were pressed out, after which 25 ml of sterilized water was added to the contents, and the resulting mixture was allowed to stand at 5° C. for 7 days while lightly shaking it several times a day. The precipitates were removed, and the filtrate was heated at 60° C. for 30 minutes, after which the filtrate was allowed to stand at 5° C. for 3 days while lightly shaking it once a day. Subsequently, the resulting precipitates were removed, and 4 ml of sterilized water containing 20% by weight of carbolic acid was added to the filtrate, after which the mixture thus obtained was allowed to stand at 5° C. for 7 days while lightly shaking it once a day. The precipitates were removed, and the pH of the filtrate was adjusted to 6.0, and the filtrate was heated at 60° C. for 30 minutes, frozen at −5° to −10° C., and then allowed to stand for 3 to 5 days. The filtrate thus treated was allowed to stand at room temperature to be gradually melted, and then filtered to obtain 25.9 ml of a slightly yellow liquid.

The solution was evaporated to dryness under reduced pressure under freezing to obtain 261 mg of a slightly yellow powder.

The above-mentioned procedures were carried out under sterile conditions.

PRODUCTION EXAMPLE 5

In a mortar were placed 1,000 poison pouches of honeybee, and their contents were pressed out, after which 25 ml of sterilized water was added to the contents. The resulting mixture was allowed to stand at 5° C. for 7 days while lightly shaking it several times a day. The resulting precipitates were removed, and the filtrate was heated at 60° C. for 30 minutes and then allowed to stand at 5° C. for 3 days while lightly shaking it once a day. Subsequently, the resulting precipitates were removed, after which 20 ml of diethyl ether was added to the filtrate, and the resulting mixture was well shaken. The ether layer was removed to obtain 43.7 ml of a slightly yellow liquid.

The above-mentioned procedures were carried out under sterile conditions.

EXAMPLE 1

The B-TL obtained in Production Example 1-(1) was diluted with the same volume of sterilized water, and then charged into ampoules each in an amount of 2 ml to prepare injections.

EXAMPLE 2

Vials were charged each with 25 mg of the B-TP obtained in Production Example 1-(2). The extract in the vials is dissolved in sterilized water when used, and employed as an injection.

EXAMPLE 3

Vials were charged with the B-TL obtained in Production Example 1-(1), and the B-TL was then freeze-dried. The freeze-dried B-TL is dissolved in sterilized water when used, and employed as an injection.

EXAMPLE 4

A mixture of the B-TP obtained in Production Example 1-(2) and Piperacillin sodium in a ratio of 25 mg: 1 g was charged into a vial and a mixture of the two in a ratio of 50 mg: 2 g was charged in another vial. The mixtures in the vials are dissolved in a physiological salt solution or a 5% by weight glucose solution when used, and employed as an injection.

EXAMPLE 5

Twenty-five milligrams of the B-TP obtained in Production Example 1-(2) and 1.0 mg of Mitomycin C were mixed, and then charged into vials. The mixture in the vials are dissolved in a physiological salt solution when used, and employed as an injection.

EXAMPLE 6

A mixture of the B-TP obtained in Production Example 1-(2) and Cefoperazone sodium in a ratio of 25 mg: 1 g was charged into a vial and a mixture of the two in a ratio of 50 mg: 2 g was charged into another vial. The mixtures in the vials are dissolved in a physiological salt solution or a 5% by weight glucose solution when used, and employed as an injection.

What is claimed is:

1. A method for treating a host mammal having a decreased immunity, comprising administering to said host mammal an immunostimulating effective amount of the deproteinized extract from the poison pouch contents of bee B-T.

* * * * *